(12) United States Patent
Opperman et al.

(10) Patent No.: US 10,111,727 B2
(45) Date of Patent: Oct. 30, 2018

(54) SURGICAL SPECIMEN MARKING MECHANISM

(71) Applicants: David Andrew Opperman, Littleton, CO (US); Robert Witkow, Denver, CO (US)

(72) Inventors: David Andrew Opperman, Littleton, CO (US); Robert Witkow, Denver, CO (US)

(73) Assignee: DB PATENT HOLDING COMPANY, LLC, Denver, CO (US)

( * ) Notice: Subject to any disclaimer, the term of this patent is extended or adjusted under 35 U.S.C. 154(b) by 161 days.

(21) Appl. No.: 15/139,012

(22) Filed: Apr. 26, 2016

(65) Prior Publication Data

US 2016/0331485 A1 Nov. 17, 2016

Related U.S. Application Data

(60) Provisional application No. 62/162,035, filed on May 15, 2015.

(51) Int. Cl.
*A61B 90/00* (2016.01)

(52) U.S. Cl.
CPC ...... *A61B 90/39* (2016.02); *A61B 2090/3937* (2016.02); *A61B 2090/3987* (2016.02); *A61B 2090/3991* (2016.02)

(58) Field of Classification Search
CPC ............ A61B 90/39; A61B 2090/3991; A61B 2090/3937; A61B 2090/3987
See application file for complete search history.

(56) References Cited

U.S. PATENT DOCUMENTS

| 5,702,128 | A  | * | 12/1997 | Maxim ................. | A61B 90/39 283/100 |
|---|---|---|---|---|---|
| 8,594,768 | B2 | * | 11/2013 | Phillips ................. | A61B 90/39 600/424 |
| 9,773,168 | B2 | * | 9/2017 | Chatow .............. | G06K 19/0614 |
| 2004/0019360 | A1 | * | 1/2004 | Farnsworth ........... | A61F 2/0063 606/151 |
| 2004/0052333 | A1 | * | 3/2004 | Sayre ..................... | A61B 90/39 378/163 |
| 2005/0234336 | A1 | * | 10/2005 | Beckman ................ | A61L 31/18 600/431 |
| 2006/0229529 | A1 | * | 10/2006 | Wright .................. | A61B 90/92 600/567 |
| 2007/0123915 | A1 | * | 5/2007 | Kammerer ............ | A61F 2/0045 606/151 |
| 2007/0270681 | A1 | * | 11/2007 | Phillips ................. | A61B 90/39 600/407 |
| 2008/0103528 | A1 | * | 5/2008 | Zirps .................. | A61B 17/0401 606/232 |
| 2009/0099588 | A1 | * | 4/2009 | Makower .............. | A61F 5/0073 606/191 |
| 2010/0187284 | A1 | * | 7/2010 | Crainich .............. | A61B 17/068 227/176.1 |

(Continued)

*Primary Examiner* — Son Dang
(74) *Attorney, Agent, or Firm* — Lewis Brisbois Bisgaard & Smith LLP; Craig W. Mueller

(57) ABSTRACT

According to one embodiment, an apparatus is disclosed. The apparatus includes an endoscopic clip placement tool and one or more marking clips attached to a specimen mass by the clip placement tool to mark a margin and orientation of the specimen mass.

12 Claims, 3 Drawing Sheets

(56) References Cited

U.S. PATENT DOCUMENTS

| | | | |
|---|---|---|---|
| 2011/0082478 A1* | 4/2011 | Glick | A61B 17/06166 606/148 |
| 2011/0184441 A1* | 7/2011 | St-Germain | A61F 2/0063 606/151 |
| 2011/0301456 A1* | 12/2011 | LeClaire | A61B 90/39 600/431 |
| 2014/0276968 A1* | 9/2014 | Miksza | A61F 2/0063 606/139 |
| 2015/0157436 A1* | 6/2015 | Bailly | A61F 2/0063 606/151 |
| 2015/0374432 A1* | 12/2015 | Godara | A61B 18/1477 606/41 |

* cited by examiner

SURGICAL SPECIMEN MARKING MECHANISM

This is a non-provisional application based on provisional application Ser. No. 62/162,035 filed on May 15, 2015 and claims priority thereof.

FIELD OF THE INVENTION

The present invention relates to medical devices, more particularly, surgical specimen margin orientation marking.

BACKGROUND

Surgical specimen margin orientation marking for endoscopic, robotic, laparoscopic, or other surgery types where body tissue is removed, is critical for pathological diagnosis, tumor excision and other margin marking. One example of surgical specimen margin orientation marking may be featured in an endoscopic excision of a tumor. In such an example, the tumor is removed and forwarded to a pathologist for evaluation by frozen or permanent section. The pathologist subsequently performs an analysis to identify malignancy at one or more margins. A surgeon may then direct additional tissue to be excised, the orientation of which is critical for proper and accurate excision.

The current technique for surgical specimen margin orientation marking involves ink marking after a specimen has been removed from a body. FIG. 1 illustrates one embodiment of a conventional marking technique in which a specimen mass is marked with a dotted line to differentiate from surrounding tissues identifies an excised mass. In such a technique an ink mark may be placed at "12:00 o'clock" position on the mass.

However, this approach is inaccurate and subject to error if the orientation of the specimen is changed (e.g., dropped, manipulated, etc.). For example, it may be difficult to find the ink marks and compare to those on the removed mass. Further, the surgeon, staff, or pathologist examining the mass may mistakenly manipulate the removed mass, or there may be miscommunication between surgeons and pathologists related to orientation. An alternative approach that may be implemented includes placement of a reference suture in the specimen at the 12:00 O'clock position. However, this approach is equally subject to error.

Accordingly, an improved surgical specimen margin orientation marking mechanism is desired.

BRIEF DESCRIPTION OF THE DRAWINGS

The present invention will be understood more fully from the detailed description given below and from the accompanying drawings of various embodiments of the invention. The drawings, however, should not be taken to limit the invention to the specific embodiments, but are for explanation and understanding only.

DETAILED DESCRIPTION

A surgical specimen margin orientation marking mechanism is described. Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 1:
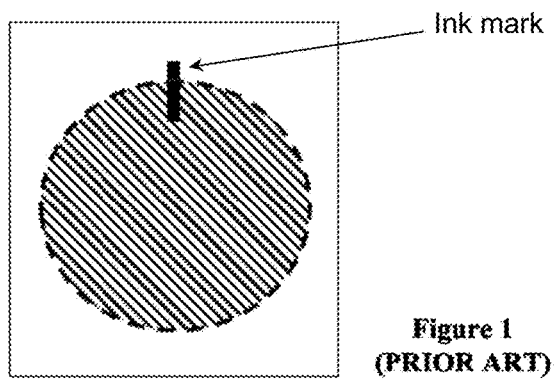
FIG. 1 illustrates a conventional surgical specimen margin orientation marking system.
Figure 2:
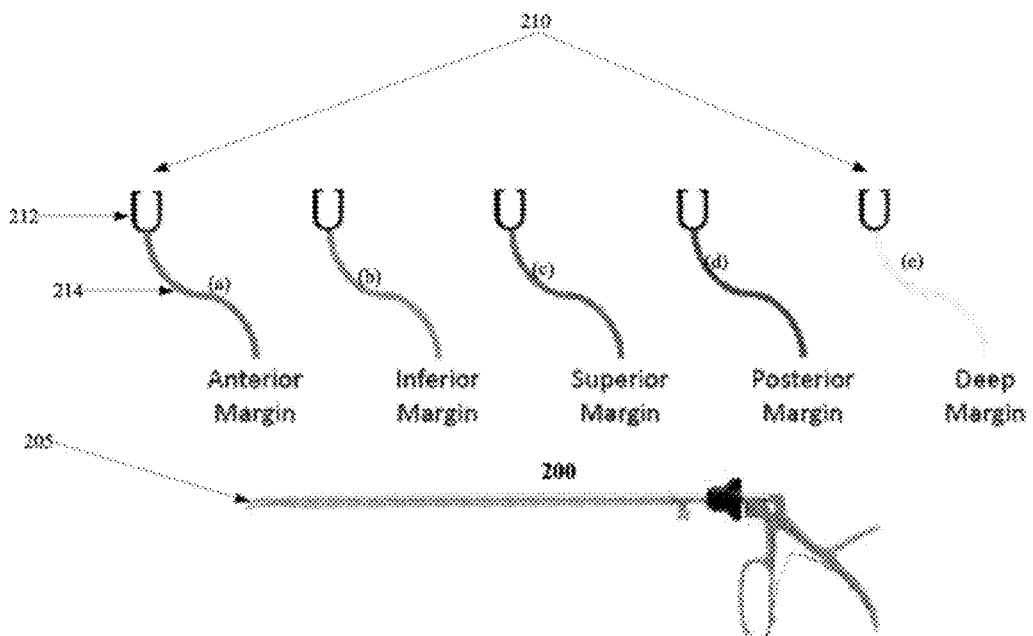
FIG. 2 illustrates one embodiment of a surgical specimen margin orientation marking mechanism.

FIG. 2 illustrates one embodiment of a surgical specimen margin orientation marking mechanism 200. Mechanism 200 includes an endoscopic clip placement tool 205 and marking clips 210. In one embodiment, each marking clip 210 includes a clip 212 and a color-coded suture 214 attached at a closed end of clip 212. In such an embodiment, clips 212 are titanium ligature clips, while the sutures are comprised of silk. However other embodiments may feature clips and sutures made of different materials, and having different shapes and weights.

According to one embodiment, the color-coded sutures 214(a)-214(e) are implemented to indicated a location. In such an embodiment, 214(a) includes a red suture indicating an anterior location. Similarly, 214(b), 214(c), 214(d) and 214(e) include green, blue, purple and yellow sutures, respectively, that represent inferior, superior, posterior and deep locations, respectively. However, other embodiments may feature various other color-coding schemes.

In one embodiment, a surgeon will place two marking clips 210 for specimen marking. In such an embodiment, one marking clip 210 is placed on a mass, while the second marking clip 210 is placed in the surrounding tissue. Subsequently, a cut is made in between the two. The result is a mirror image marking of the two pieces.

Figure 3A:
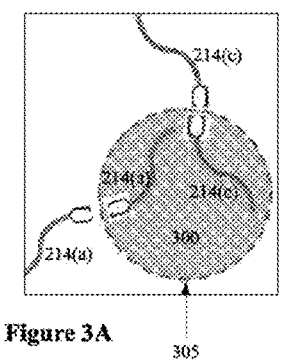
FIGS. 3A-3E illustrate embodiments of a mass identified by marking clips.

Color coded sutures 214 are attached to the clips having colors designating the anterior, inferior, superior, posterior, and deep margins, as discussed above. FIGS. 3A-3E illustrate embodiments of a mass identified by marking clips 210. As shown in FIG. 3A, a mass 300 to be excised is identified by dotted line 305 to differentiate from surrounding tissues.

Figure 3B:
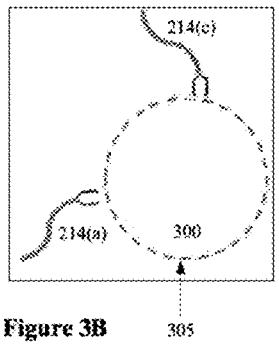
Figure 3C:
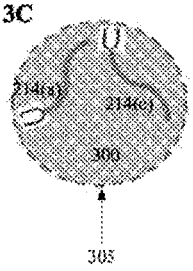

Color-coded sutures 214 devices are placed on the margins to identify orientation. For instance, clips 210 are shown having pairs of sutures 214(a) and 214(c). Note that only two types of suture 214 clips have been shown for ease of viewing. FIG. 3B shows clips 210 having sutures 214(a) and 214(b) attached to tissue above mass 300 for orientation following excision of mass 300, while FIG. 3C shows clips 210 having sutures 214(a) and 214(b) attached to mass 300 for orientation following excision.

Figure 3D:
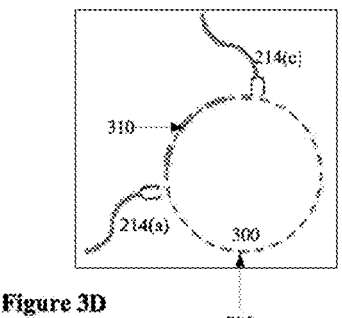
Figure 3E:
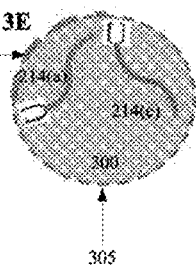

According to one embodiment, marking mechanism 200 enables accurate communication between a pathologist and a surgeon, assuming a positive or close margin determined by the pathologist. FIG. 3D shows additional tissue 310 requiring excision that can be more accurately addressed, and FIG. 3E shows a positive or close margin identified by the pathologist.

Figure 4:
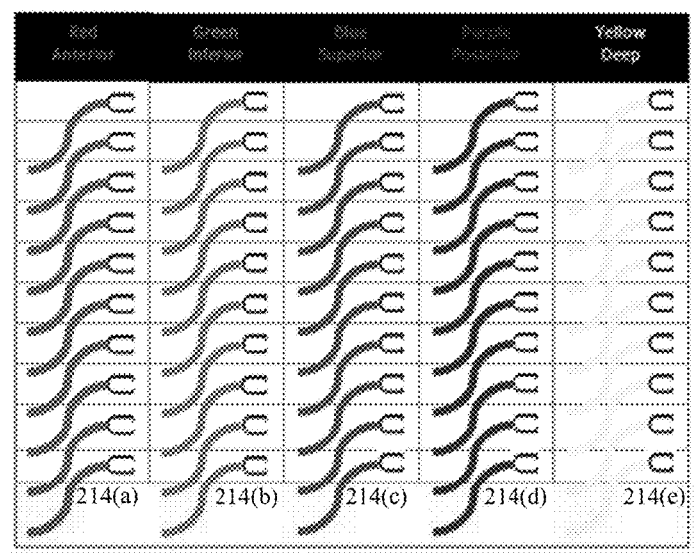
FIG. 4 illustrates one embodiment of a package of marking clips.

In a further embodiment, the surgeon may implement the clip 210/suture 214 combination as an effective tool for manipulating tissues, which is more efficient than attaching a handle to an otherwise slippery surface. FIG. 4 illustrates one embodiment of a package of marking clips. As shown in FIG. 4, a package may include 25-pair/50-unit cassette of clips 210 having the various sutures 214 for endoscopic procedures.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. An apparatus comprising:
   an endoscopic clip placement tool;
   a first marking clip adapted to be attached with the clip placement tool to a first area associated with a specimen mass, the specimen mass having an outer margin that defines the shape of the specimen mass;
   a second marking clip adapted to be attached to a second area associated with tissue surrounding the specimen mass and outside the margin; and
   wherein the first area and the second area are located on direct opposite sides of the margin, such that the first marking clip and the second marking clip identify the orientation of the specimen mass relative to the tissue surrounding the specimen mass.

2. The apparatus of claim 1, wherein the first marking clip and the second marking clip comprise:
   a closed end; and
   a suture attached to the closed end.

3. The apparatus of claim 2, wherein a suture color of the first marking clip and a suture color of the second marking clip are identical.

4. The apparatus of claim 3, further comprising:
   a third marking clip adapted to be attached to a third area associated with the specimen mass;
   a fourth marking clip adapted to be attached to a fourth area associated with the surrounding tissue;
   wherein the third marking clip and the fourth marking clip comprise:
      a closed end; and
      a suture attached to the closed end;
   wherein the suture color of the first marking clip and the suture color of the second marking clip is a first color;
   wherein a suture color of the third marking clip and a suture color of the fourth marking clip is a second color that is different from the first color; and
   wherein the first marking clip and the second marking clip identify a first position of the margin and the third marking clip and the fourth marking clip identify a second position of the margin.

5. The apparatus of claim 4, wherein the first position is associated with an anterior area of the margin, an inferior area of the margin, a superior area of the margin, a posterior area of the margin, or a deep area of the margin; and
   wherein the second position is associates with an anterior area of the margin, an inferior area of the margin, a superior area of the margin, a posterior area of the margin, or a deep area of the margin, but which is different from the area of the margin associated with the first portion.

6. The apparatus of claim 1, wherein the first marking clip is configured to manipulate the mass specimen.

7. The apparatus of claim 1, wherein the first marking clip and the second marking clip are not interconnected.

8. A marking system comprising:
   a first marking clip adapted to be attached to a first location of a specimen mass, the outer boundary of which is defined by an outer margin;
   a second marking clip that is distinct from the first marking clip that is adapted to attach to a second location associated with tissue surrounding the specimen mass, and
   wherein the first location and the second location are located on direct opposite sides of the margin, which orients the specimen mass relative to the surrounding tissue.

9. The marking system of claim 8, wherein the first marking clip and second marking clip comprise a closed end with an identifier extending therefrom.

10. The marking system of claim 9, wherein the identifier has a color that corresponds to a location of the first marking clip along the margin, and wherein the color is different if the location is associated with an anterior area of the margin, an inferior area of the margin, a superior area of the margin, a posterior area of the margin, or a deep area of the margin.

11. The marking system of claim 10, wherein the color associated with the anterior area is red, the color associated with the inferior area is green, the color associated with the superior area is blue, and the color associated with the posterior location is purple.

12. The marking system of claim 8, wherein the first marking clip is configured to manipulate the mass specimen.

* * * * *